US011291777B2

(12) United States Patent
Toennesen et al.

(10) Patent No.: US 11,291,777 B2
(45) Date of Patent: Apr. 5, 2022

(54) NEEDLE CANNULA, AN INJECTION NEEDLE ASSEMBLY FOR AN INJECTION DEVICE AND AN INJECTION DEVICE COMPRISING SUCH ASSEMBLY

(71) Applicant: Novo Nordisk A/S, Bagsvaerd (DK)

(72) Inventors: Lene Westergaard Toennesen, Alleroed (DK); Erik Pedersen, Taars (DK); Ejnar Laustsen, Broenderslev (DK)

(73) Assignee: Novo Nordisk A/S, Bagsvaerd (DK)

( * ) Notice: Subject to any disclaimer, the term of this patent is extended or adjusted under 35 U.S.C. 154(b) by 216 days.

(21) Appl. No.: 16/473,948

(22) PCT Filed: Dec. 28, 2017

(86) PCT No.: PCT/EP2017/084696
§ 371 (c)(1),
(2) Date: Jun. 26, 2019

(87) PCT Pub. No.: WO2018/122295
PCT Pub. Date: Jul. 5, 2018

(65) Prior Publication Data
US 2019/0336703 A1 Nov. 7, 2019

(30) Foreign Application Priority Data

Dec. 30, 2016 (EP) .................................... 16207643

(51) Int. Cl.
*A61M 5/32* (2006.01)
*A61M 5/24* (2006.01)
(52) U.S. Cl.
CPC ........ *A61M 5/3286* (2013.01); *A61M 5/2422* (2013.01); *A61M 5/2459* (2013.01);
(Continued)

(58) Field of Classification Search
CPC .... A61M 5/24; A61M 5/3286; A61M 5/2466; A61B 17/06066
See application file for complete search history.

(56) References Cited

U.S. PATENT DOCUMENTS 2,716,983 A  9/1955 Windischman et al.
3,071,135 A  1/1963 Baldwin et al.
(Continued)

FOREIGN PATENT DOCUMENTS

CN  1596138 A  3/2005
CN  102573966 A  7/2012
(Continued)

*Primary Examiner* — Laura A Bouchelle
(74) *Attorney, Agent, or Firm* — Wesley Nicolas (57) ABSTRACT

A needle cannula for an injection device, extends along a central axis and comprises: a) a skin piercing distal end (133b), b) a proximal end (133a) configured for penetrating a seal structure (102b) of a medicament container (102), and c) a sidewall extending between the skin piercing distal end (133b) and the proximal end (133a), wherein the proximal end (133a) is defined by an angled surface (134) pointing proximally, the angled surface (134) defining a leading portion (134.1) and a heel portion (134.2), and wherein the angled surface (134) comprises a surface portion (134a, 134b) at the heel portion (134.2) forming an angle ($\alpha_1$) between 50 to 75 degrees with respect to the central axis, and further comprises a surface portion (134c) at the leading portion (134.1) forming an angle ($\alpha_2$) between 60 to 85 degrees with respect to the central axis. An injection needle assembly for an injection device and an injection device comprising such assembly are further described.

38 Claims, 5 Drawing Sheets

(52) U.S. Cl.
CPC ........ *A61M 5/3202* (2013.01); *A61M 5/3245* (2013.01); *A61M 2005/2481* (2013.01)

(56) References Cited

U.S. PATENT DOCUMENTS

| | | | | |
|---|---|---|---|---|
| 5,169,602 | A | * 12/1992 | Pang | .......................... A61J 1/20 |
| | | | | 215/247 |
| 5,536,249 | A | * 7/1996 | Castellano | ............. G16H 20/17 |
| | | | | 604/65 |
| 5,709,668 | A | 1/1998 | Wacks | |
| 5,716,348 | A | 2/1998 | Marinacci et al. | |
| 5,733,266 | A | 3/1998 | Gravlee, Jr. | |
| 6,517,523 | B1 | * 2/2003 | Kaneko | ............... A61M 5/3286 |
| | | | | 163/5 |
| 6,855,129 | B2 | 2/2005 | Jensen et al. | |
| 9,642,970 | B2 | 5/2017 | Shaw et al. | |
| 9,833,579 | B2 | * 12/2017 | Pedersen | ............. A61M 5/3287 |
| 2002/0188247 | A1 | 12/2002 | Peery | |
| 2017/0144177 | A1 | 5/2017 | Heldt et al. | |
| 2017/0259285 | A1 | 9/2017 | Petit | |

FOREIGN PATENT DOCUMENTS

| | | | |
|---|---|---|---|
| FR | 3029810 | A1 | 6/2016 |
| JP | 3030963 | U | 11/1996 |
| WO | 2004054643 | A1 | 7/2004 |
| WO | 2015197866 | A1 | 12/2015 |
| WO | 2016001601 | A1 | 1/2016 |
| WO | 2016116614 | A1 | 7/2016 |

* cited by examiner

NEEDLE CANNULA, AN INJECTION NEEDLE ASSEMBLY FOR AN INJECTION DEVICE AND AN INJECTION DEVICE COMPRISING SUCH ASSEMBLY

CROSS-REFERENCE TO RELATED APPLICATIONS

This application is a 35 U.S.C. § 371 National Stage application of International Application PCT/EP2017/084696 (published as WO 2018/122295), filed Dec. 28, 2017, which claims priority to European Patent Application 16207643.4, filed Dec. 30, 2016, the contents of all above-named applications are incorporated herein by reference.

FIELD OF THE INVENTION

The present invention relates to a needle cannula, an injection needle assembly and an injection device for injecting a medicament comprising such an injection needle assembly.

BACKGROUND OF THE INVENTION

Within development of medical devices it is of primary focus to develop devices that are safe. Yet it is also of particular concern that the medical devices are as simple and user-friendly as possible. Within medical injectors, such as auto-injectors, it is an aim that it involves no or little needle handling. Before use the needle must be kept sterile.

In some injection devices, the needle is protected by a needle cover, for example a resilient pierceable needle cover, which maintains a sterile barrier around the needle itself. Such needle cover is often assembled together with the needle to form a needle assembly. WO 2015/197866 A1 and WO 2016/116614 A1 disclose medicament injectors which incorporate a pair of flexible pierceable needle covers that prior to use maintains a front needle and a rear needle in a sterile state. By using a flexible pierceable needle cover as sterility barrier the needle can penetrate the sterility barrier thereby obviating the need for removing the needle cover prior to commencing the actual injection procedure. This eases the needle handling significantly.

When using septum equipped cartridges and separate needles which, upon initial use, penetrates the septum to establish fluid communication, there is a risk that coring of the septum will occur. U.S. Pat. No. 2,716,983 discloses various piercing needles where the needle tip is provided with a design to inhibit coring. Further, U.S. Pat. No. 5,716,348 discloses a needle with a design where the cylindrical wall has a laterally facing opening spaced from a rearward opening, and wherein a restriction is arranged between the rearward opening and the laterally facing opening. U.S. Pat. No. 5,709,668 discloses an automatic injector employing a non-coring needle having side port geometry to minimize or eliminate coring of a rubber seal or septum when impaled by the internal needle tip of the cannula.

Having regard to the above-identified prior art devices, it is an object of the present invention to provide an improved needle cannula, to provide an injection needle assembly including such needle cannula and an injection device comprising such injection needle assembly, wherein the design of the needle cannula minimizes the risk of coring.

BRIEF DESCRIPTION OF THE INVENTION

In a first aspect the present invention relates to a needle cannula for an injection device, wherein an elongated tubular needle cannula extends along a central axis and comprises:

a skin piercing distal end,
a proximal end arranged axially opposite the skin piercing distal end, the proximal end being configured for penetrating a seal structure of a medicament container,
a sidewall extending between the skin piercing distal end and the proximal end, and
a lumen extending through the needle cannula along said central axis, said lumen has a first opening arranged axially at the skin piercing distal end and a second opening arranged axially at the proximal end, wherein the proximal end being defined by an angled surface pointing generally proximally, the angled surface intersecting with the sidewall at a proximal-most point defining a leading portion and intersecting with the sidewall at an oppositely arranged trailing portion defining a heel portion.

The angled surface pointing generally proximally comprises a first surface portion at the heel portion where the first surface portion includes surface areas that form an angle ($\alpha_1$) between 50 to 75 degrees with respect to the central axis. The angled surface pointing generally proximally further comprises a second surface portion at the leading portion where the second surface portion includes surface areas forming an angle ($\alpha_2$) between 60 to 85 degrees with respect to the central axis.

In accordance with the first aspect, the needle cannula enables penetration of a cooperating sealing element in a way wherein a slightly angled bevel surface at the leading portion of the needle cannula enables the leading portion of the needle cannula to provide a well-defined contact point for the needle cannula to establish a connection with the cooperating sealing element. At the same time, as the first surface portion at the heel portion includes surface areas that form an angle ($\alpha_1$) that is smaller than the angled bevel surface at the leading portion of the needle cannula, the leading portion extends quite far relative to the heel portion. This enables the leading portion to puncture or start rupturing the sealing element before the heel portion is brought to force its way through the sealing element. Hence, a particular safe penetration is enabled providing no or only little risk of coring of the sealing element during penetration.

In some embodiments, the surface areas of the first surface portion forming an angle ($\alpha_1$) between 50 to 75 degrees with respect to the central axis constitute at least 20% of the total area of said angled surface. Also, in some embodiments, the surface areas of the second surface portion forming an angle ($\alpha_2$) between 60 to 85 degrees with respect to the central axis constitute at least 30% of the total area of said angled surface.

In further embodiments said angled surface intersects with the sidewall to define a radially inwards facing circumferential edge and a radially outwards facing circumferential edge. The radially inwards facing circumferential edge and/or the radially outwards facing circumferential edge may in some embodiments be formed with blunted non-incising edges along an annular section symmetrically disposed around the heel portion. In some embodiments, the annular section having such blunt edges may have an annular width within 100 to 220 degrees, i.e. within 50 to 110 degrees in either circumferential direction from the heel portion. In other embodiments, the annular section may have an annular width within 140 to 190 degrees.

The edges arranged at the leading portion may be formed so that these edges are sharpened.

In exemplary embodiments, the surface portion at the leading portion forms an angle ($\alpha_2$) with respect to the central axis which is 5 to 10 degrees greater than the angle ($\alpha_1$) of the surface portion at the heel portion.

In further exemplary embodiments, said surface portion at the heel portion forms an angle ($\alpha_1$) between 55 to 70 degrees with respect to the central axis.

The needle cannula may in some embodiments be configured for subcutaneous injection, with the size of the needle cannula being a 26 G needle or smaller, preferably a 27 G needle, more preferably a 28 G needle, more preferably a 29 G needle and most preferably a 30 G needle.

In still further embodiments, the sidewall of the needle cannula forms an elongated tubular enclosure that does not include opening(s) other than said first opening and said second opening.

In a second aspect the present invention relates to a needle cannula for an injection device, wherein an elongated tubular needle cannula extends along a central axis and comprises:
- a skin piercing distal end,
- a proximal end arranged opposite the skin piercing distal end, the proximal end being configured for penetrating a seal structure of a medicament container,
- a sidewall extending between the skin piercing distal end and the proximal end, and
- a lumen extending through the needle cannula along said central axis, said lumen has a first opening arranged axially at the skin piercing distal end and a second opening arranged axially at the proximal end, wherein the proximal end is defined by an angled surface pointing proximally, wherein at least 60% of the surface portions of the angled surface form an angle ($\alpha$) between 70 degrees to 85 degrees with respect to the central axis.

In accordance with the second aspect, the needle cannula enables penetration of a cooperating sealing element in a way wherein a slightly angled bevel surface of the needle cannula enables a leading portion of the needle cannula to provide a well-defined contact point for the needle cannula to establish a connection with the cooperating sealing element. Hence, a particular safe penetration is enabled providing no or only little risk of coring of the sealing element during penetration.

In some embodiments at least 60% of the surface portions of the angled surface form an angle ($\alpha$) between 76 degrees to 84 degrees with respect to the central axis.

In further embodiments the angled surface intersects with the sidewall at a proximal-most point defining a leading portion and intersects with the sidewall at an oppositely arranged trailing portion defining a heal portion, wherein the angled surface of the heal portion forms an angle ($\alpha$) between 70 degrees to 85 degrees with respect to the central axis, preferably between 76 degrees to 84 degrees with respect to the central axis.

In particular embodiments, the heal portion is formed with edges that are blunted. In further embodiments, all circumferential edges at the proximal end of the needle cannula are formed with blunted edges.

In further exemplary embodiments, the entire angled surface of the proximal end of the needle cannula forms an angle ($\alpha$) with respect to the central axis between 70 degrees to 85 degrees, preferably between 76 degrees to 84 degrees with respect to the central axis.

The said angled surface may in some embodiments be provided as a single planar angled cut tip.

The needle cannula may in some embodiments be configured for subcutaneous injection, with the size of the needle cannula being a 26 G needle or smaller, preferably a 27 G needle, more preferably a 28 G needle, more preferably a 29 G needle and most preferably a 30 G needle.

In still further embodiments, the sidewall of the needle cannula forms an elongated tubular enclosure that does not include opening(s) other than said first opening and said second opening.

In a third aspect the invention relates to an injection needle assembly incorporating a needle cannula according to any one of the first aspect and the second aspect.

The injection needle assembly may be formed to comprise:
- a needle hub,
- an elongated tubular needle cannula in accordance with any of the first or the second aspect, and
- a first needle cover, wherein the needle hub holds the needle cannula between the skin piercing distal end and the proximal end such that a distal portion of the needle cannula extends distally from the needle hub and such that a proximal portion of the needle cannula extends proximally from the needle hub towards the proximal end of the needle cannula, and wherein the first needle cover is mounted on the needle hub and forms an axially extending elongated flexible enclosure which sealingly accommodates the proximal portion of the needle cannula, wherein the first needle cover has a needle hub end mounted relative to the needle hub and a free end extending beyond the proximal end of the needle cannula, the first needle cover being configured to axially collapse and become penetrated by the proximal portion of the needle cannula when a distally directed penetration force is applied on the free end of the first needle cover urging the free end of the first needle cover towards the needle hub.

In further embodiments, the injection needle assembly may further comprise a second needle cover, wherein the second needle cover is mounted on the needle hub and forms an axially extending elongated flexible enclosure which sealingly accommodates the distal portion of the needle cannula, wherein the second needle cover has a needle hub end mounted relative to the needle hub and a free end extending beyond the distal end of the needle cannula, the second needle cover being configured to axially collapse and become penetrated by the distal portion of the needle cannula when a proximally directed penetration force is applied on the free end of the second needle cover urging the free end of the second needle cover towards the needle hub.

In particular embodiments, the first needle cover and/or the second needle cover may be made from silicone rubber.

In a fourth aspect the invention relates to an injection device incorporating a needle assembly according to the third aspect.

The injection device may be formed to comprise:
- a housing defining a distal drug expelling end and an opposite proximal end,
- an injection needle assembly in accordance with the third aspect, the injection needle assembly arranged relative to the housing with the proximal end of the needle cannula pointing towards the proximal end of the housing,
- a cartridge containing a medicament, the cartridge comprising a cylindrical body extending along a longitudinal axis arranged coaxially with the central axis of the needle cannula, the cartridge further comprising a seal structure adapted to become penetrated by the proximal portion of the needle cannula enabling expelling of medicament from the cartridge, wherein the cartridge is arranged axially movable relative to the injection needle assembly for moving the cartridge from a first state where the first needle cover and the seal structure are not penetrated by the needle cannula and into a second state where the proximal portion of the needle cannula has penetrated the first needle cover and the seal structure, and an expelling assembly comprising a strained spring configured to act on the cartridge, wherein the expelling assembly is activatable to enable the strained spring to move the cartridge from the first state to the second state.

The injection device may be so configured that, upon activation of the expelling assembly, the proximal end of the needle cannula penetrates the seal structure of the medicament container by a relative axial movement with no relative rotation between the needle cannula and the seal structure.

In some embodiments, the seal structure of the medicament container and the first needle cover abuts each other during penetration by the proximal end of the needle cannula.

In further embodiments the injection needle assembly comprises a second needle cover as described in connection with the third aspect. Such injection device may be formed to comprise a needle shield arranged to shield the second needle cover, and wherein the needle shield and the injection needle assembly is arranged to axially move relative to each other for causing the distal portion of the needle cannula to penetrate the second needle cover and enable the distal portion of the needle cannula to extend beyond a distal end portion of the needle shield.

In further embodiments, the seal structure comprises a cartridge septum arranged in a plane substantially orthogonal to the longitudinal axis.

In still other embodiments, the seal structure of the cartridge is provided as, or comprises, a non-slit cartridge septum.

In certain embodiments the injection device is formed as an auto-injector that is activated or triggered by relative movement between the needle shield and the injection needle assembly. The auto-injector may be configured so that a front part of the needle is inserted manually into an injection site by holding the needle shield against an injection site and applying a manual force for moving the needle forward relative to the needle shield such as to cause the front needle to firstly penetrate the second needle cover covering the front part of the needle and subsequently insert the front needle into the injection site.

The needle shield may thus be configured to act on the second needle cover for causing the second needle cover to become penetrated by distal portion of the needle cannula. In particular embodiments, the needle shield engages, as it is being moved axially relative to the needle cover, the second needle cover and thus forces the free end of the second needle cover to move relative to the needle cannula which in turn causes the needle cover to become penetrated by the distal portion of the needle cannula.

In certain embodiments, the auto-injector is configured for being triggered upon the distal portion of the needle cannula reaching a pre-defined penetration depth. Such triggering is facilitated by the user manually pushing the auto-injector against the injection site.

It should be emphasized that the term "comprises/comprising/comprised of" when used in this specification is taken to specify the presence of stated features, integers, steps or components but does not preclude the presence or addition of one or more other features, integers, steps, components or groups thereof.

As used herein, the term "medicament" is meant to encompass any flowable drug capable of being passed through a delivery means such as a hollow needle or cannula in a controlled manner. Examples of flowable drugs are a liquid, a solution, a gel or a fine suspension. Also lyophilized drugs which prior to administration are dissolved into a liquid form are encompassed by the above definition. Representative medicaments includes for example pharmaceuticals, peptides, proteins (e.g. insulin, insulin analogues and C-peptide), hormones, biologically derived or active agents, hormonal and gene based agents, nutritional formulas and other substances in both solid (dispensed) or liquid form.

BRIEF DESCRIPTION OF THE DRAWINGS

In the following, the invention will be described in greater detail with reference to embodiments shown by the enclosed figures. It should be emphasized that the embodiments shown are used for example purposes only and should not be used to limit the scope of the invention.

DETAILED DESCRIPTION OF THE EMBODIMENTS

FIGS. 1 to 4 illustrate operational states for an example injection device which is suitable for use in connection with the present invention. The injection device is shown in four different states of operation in order to explain the basic function of the device. The shown device is generally similar to the device disclosed in WO 2015/197866 A1 in connection with FIGS. 1c, 2c, 3c and 5c of said document. For a detailed description of the disclosed device reference is made to the WO document.

It is to be noted that the shown injection device forms a suitable but non-limiting example and that the needle cannula and injection needle assembly of the present invention can be used together with other types of injection devices.

All the details of the shown injection device will not be described in detail herein since these details have already been described in the above WO document.

FIGS. 1 to 4 show an injection device 1 with a medicament containing cartridge 2, an injection needle provided as a needle cannula 3 having a proximal end 3a and a distal end 3b, a needle hub 4, a needle shield 5, a housing 6 and an expelling assembly 7. The details of the expelling assembly will only be described in general terms in this specification since the needle assembly of the present invention will work with many different types of expelling assemblies.

Figure 1:
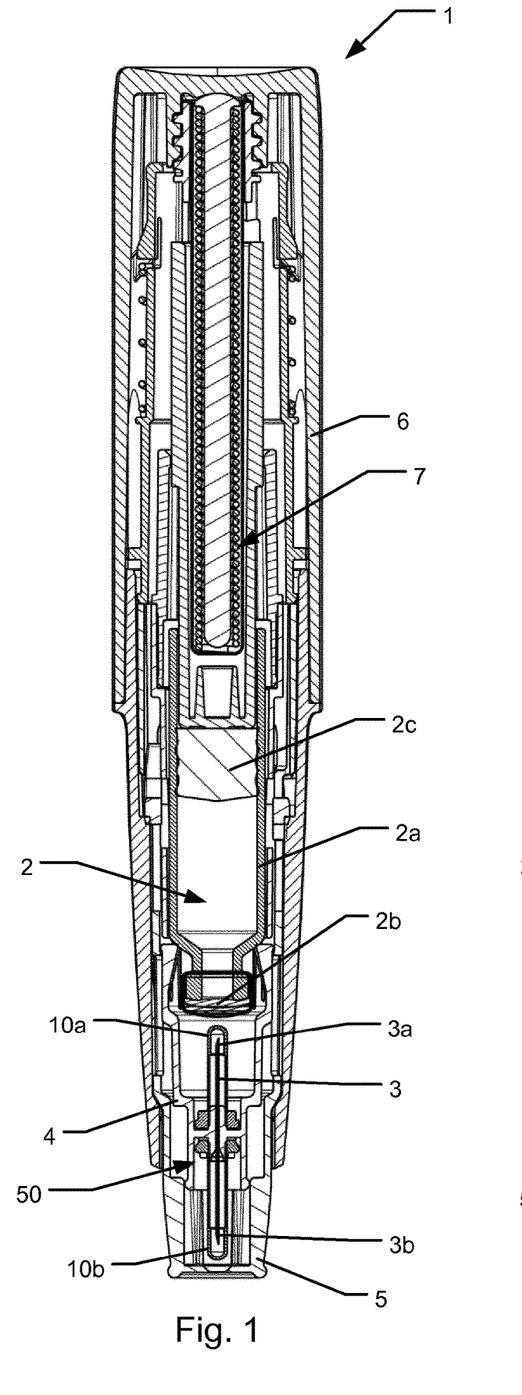
FIG. 1 shows a sectional side view of one example of an injection device suitable for incorporation of a needle assembly in accordance with the present invention, the needle assembly being in an initial shielded state.

In the shown embodiment, in the shielded state as shown in FIG. 1, the distal end of the needle shield 5 is arranged distally to the distal end 3b of the needle cannula. In this way, the needle is completely shielded by the needle shield. It can also be seen that in the current embodiment, the needle shield 5 is a single element which completely encases the needle assembly.

As can be seen from FIG. 1, the needle 3 is arranged as a needle cannula having two pointed ends, one arranged at the proximal end of the needle cannula and one arranged at the distal end. The needle hub 4 grips the middle portion of the needle cannula 3 so that both the distal and the proximal ends of the needle protrude axially relative to the hub 4, i.e. respectively forming a front needle and a rear needle. In the shown embodiment, the hub 4 is mounted fixedly relative to the housing 6. During use, the proximal end of the needle 3a is arranged to engage with a container 2 containing the medicament which is to be injected while the distal end 3b is arranged to pierce the skin of the user to inject the medicament into the body of the user.

In the shown embodiment, the container 2 forms a cartridge with a body 2a having a distally arranged outlet covered by a seal structure in the form of a cartridge septum 2b adapted to be pierced by a needle cannula for establishing fluid communication with the cartridge interior. The body of the cartridge accommodates a slidably arranged piston 2c. In the state where a needle has pierced cartridge septum 2b, piston 2c is drivable towards the outlet in order to dispense medicament from the cartridge 2.

As can also be seen from FIG. 1, the proximal end 3a of the needle is covered by a proximal needle cover 10a forming a flexible pierceable needle cover and the distal end of the needle 3b is covered by a distal needle cover 10b also forming a flexible pierceable needle cover. The needle covers 10a and 10b will also be referred to as a rear cover and front cover, respectively. Likewise, the part of the needle cannula that extends in a proximal direction from the hub will be referred to as the rear needle, whereas the part of the needle cannula extending in a distal direction from the hub will be referred to as the front needle. It is to be noted that in FIGS. 1 to 4 the shape of the needle covers 10a and 10b are only schematically depicted. The rear and front needle covers 10a and 10b are arranged to allow the needle to be sterilized and then ensure that the needle itself is not contaminated by further handling of the needle assembly.

Figure 2:
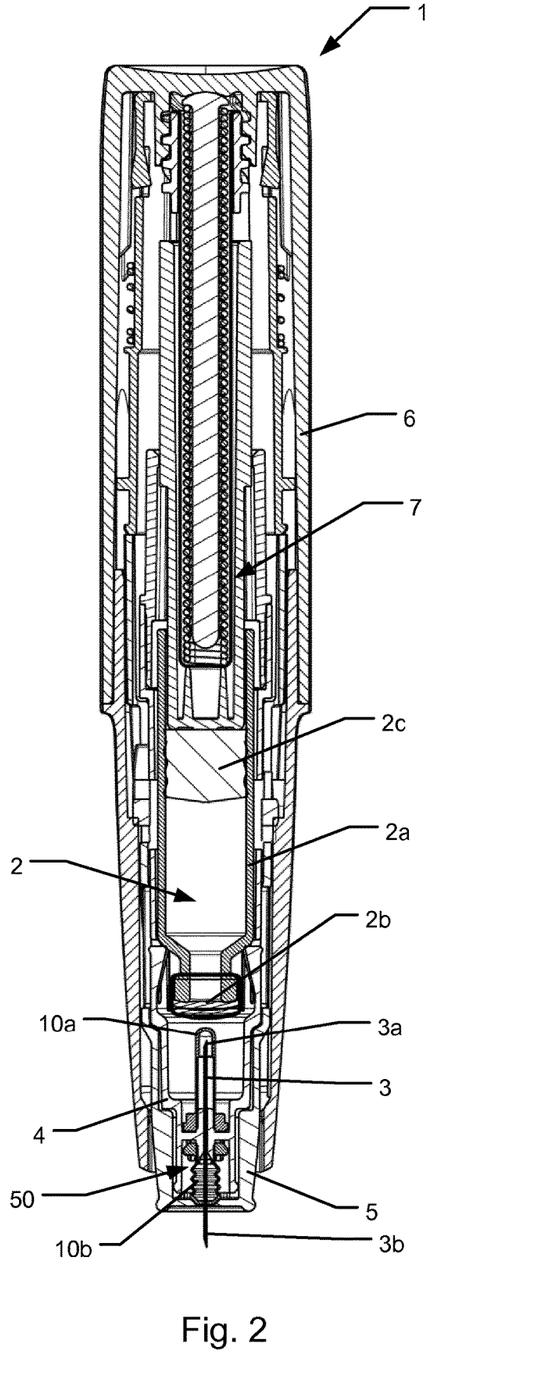
FIG. 2 shows a sectional side view of the injection device of FIG. 1 in a state where the distal end of the needle fully protrudes from a needle shield.

In FIG. 2, the needle shield 5 has been retracted with respect to the needle hub 4 such that the distal end 3b of the needle now extends distally past the distal end 5b of the needle shield. In this way the distal end of the needle 3b is now exposed and ready for fluid communication with a user. As can also be seen in FIG. 2, the act of retracting the needle shield has caused the distal needle cover 10b to be pulled back. This causes the distal end of the needle to pierce through the needle cover thereby uncovering the distal end of the needle. Due to the flexible nature of the needle cover, the needle cover is easily retracted.

Figure 3:
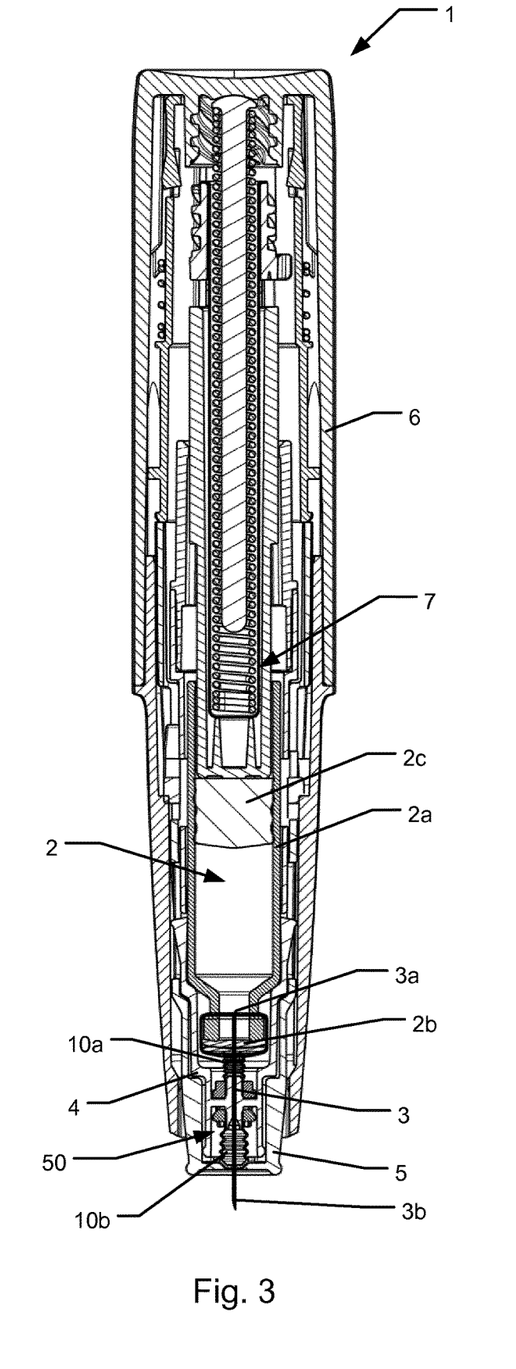
FIG. 3 shows a sectional side view of the injection device of FIG. 1 in a state where a cartridge has been connected to the proximal end of the needle for fluid delivery and wherein expelling has been initiated.

In the shown embodiment, the act of retracting the needle shield relative to the needle hub triggers the device and thus activates the expelling assembly 7. The expelling assembly primarily consists of a plunger which is biased distally by a force provided by a compression spring. Prior to triggering the compression spring is in a pre-tensed state where the plunger is retained axially by a retaining mechanism. Upon triggering, the plunger is axially released and urged forward by the energy released from the compression spring. The plunger then exerts a distally directed force onto the piston 2c of the cartridge 2. In the shown device, the plunger of the expelling assembly 7 provides a force which initially moves the cartridge 2 relative to the housing 6 and subsequently moves the piston 2c in the cartridge 2 so that the a dose of the medicament in the cartridge 2 is expelled through the needle assembly 50. In FIG. 3, it can be seen that the expelling assembly 7 has pushed the medicament containing cartridge 2 forward in a distal direction to engage with the proximal end of the needle. The proximal end of the needle punctures the septum 2b of the cartridge thereby establishing a fluid path from the cartridge through the needle and to the distal end of the needle whereby the medicament can be injected into the user at the selected injection site. As can also be seen in FIG. 3, the proximal needle cover 10a has also been compressed by the motion of the cartridge towards the needle. This thereby uncovers the proximal end of the needle and allows it to engage with the cartridge.

Figure 4:
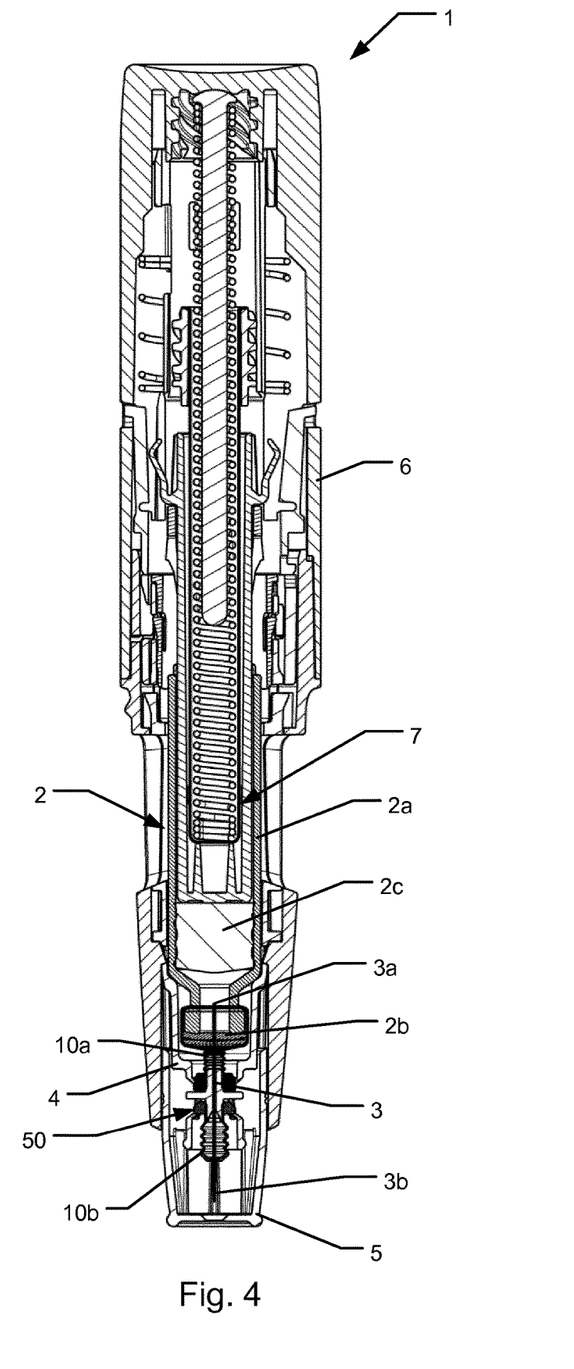
FIG. 4 shows a sectional side view of the injection device of FIG. 1 in a state where the needle shield has returned to its original position to put the needle into a shielded state again.

In FIG. 4, the expelling assembly has pushed the piston 2c arranged in the cartridge distally, thereby causing the medicament in the cartridge to be injected through the needle into the injection site. After the medicament has been injected, the needle shield is again pushed forward with respect to the needle hub to shield the distal end of the needle. In the shown embodiment, this occurs as a consequence of the user manually retracting the housing 6 of the injection device relative to the injection site. In the shown embodiment, the needle shield 5 is biased in the distal direction by means of a needle shield spring.

The description above with respect to FIGS. 1 to 4 has been provided to give background information of the use of an exemplary injection device. The injection device described is one of many different available injection devices. It should be noted that the needle cannula and the injection needle assembly of the current invention can be used with different types of injection devices wherein a septum equipped cartridge is cooperating with a separate needle assembly, not just the one described above with respect to FIGS. 1 to 4.

Figure 5:
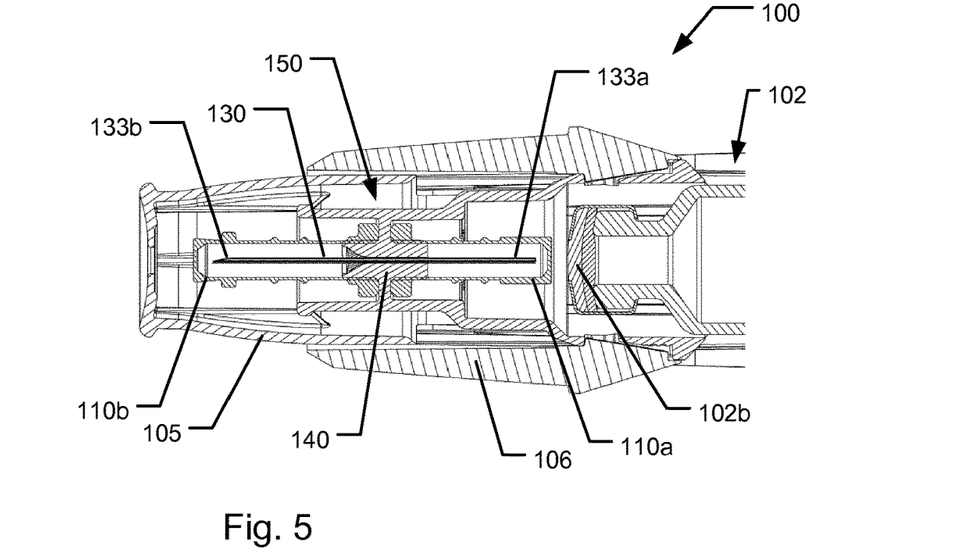
FIG. 5 shows a cross sectional side view of the front portion of a first embodiment of an injection device incorporating a needle assembly according to the invention.

FIG. 5 shows a cross sectional detailed view of a distal portion of an injection device similar to the injection device shown in FIGS. 1-4, but incorporating an embodiment of a needle assembly 150 in accordance with an aspect of the present invention. The proximal needle cover 110a is formed similar to the needle cover 10 shown in FIGS. 11a-11d of WO 2016/116614 A1.

Tests have shown that for conventional double pointed needles, due to particular conditions during triggering of the device, there is a risk that the proximal portion of the needle cannula 130, as it penetrates through the proximal needle cover 10a and the cartridge septum 2b, generates cut-out cores of material of the needle cover 10a and/or the cartridge septum 2b. It has been shown that the risk is most noticeable with high connecting velocities during penetration but also when penetration occurs in low ambient temperatures corresponding to temperatures used during long-time storage of medicament, e.g. refrigerator temperature.

Detailed tests have been performed with different samples of an example 30 G needle cannula having a proximal portion with a beveled surface provided as a planar angular cut that forms an angle of 28 degrees with the central axis of the needle cannula. Individual penetration tests have been performed with such example 30 G needle cooperating only with the proximal needle cover 10a, i.e. without cooperating with a cartridge septum, but also with such example 30 G needle cooperating only with the cartridge septum, i.e. without cooperating with the proximal needle cover 10a. All tests have been performed at an ambient temperature of 5 deg. Celsius and with a penetration speed corresponding to the speed obtained by triggering an auto-injector such as shown in FIGS. 1-4. In both situations the example 30 G needle has performed acceptably with no traces of fracturing of the needle cover and the cartridge septum, respectively. However, in a real-life setup corresponding to the configuration shown in FIGS. 1-4 wherein the needle assembly including the example 30 G needle is incorporated in an autoinjector having both a needle cover 10a and a cartridge septum 2b, traces of fracturing elements have been observed. Most likely, the effect of coring in such setup is likely to be associated with the interfacing forces between the needle cover 10a and the septum 2b during needle cannula penetration.

Further detailed tests have been performed with an example needle cannula having a proximal portion with an end surface provided as a planar angular cut forming a 90 degree angle with the central axis of the needle cannula, and wherein all edges at the proximal end of the needle cannula subsequently have been made smooth by polishing. Such blunt needle cannula performs acceptably in a setup where the needle cannula only cooperates with a cartridge septum. However, in a real-life setup corresponding to the configuration shown in FIGS. 1-4 wherein the needle assembly including the example blunt needle with a 90 degree cut is incorporated in an autoinjector having both a needle cover 10a and a cartridge septum 2b, traces of fracturing elements have been observed.

In accordance with the present invention a plurality of different needle cannulas of needle gauge 27 G and 30 G have been prepared wherein each of the needle cannulas have been formed by cutting the proximal end at an angle (α) with respect to the central axis of the needle cannula. A large number of sample needle cannulas have been prepared by cutting the proximal portion of the needle cannula to provide a bevel surface having an angle (α) relative to the central axis of the needle cannula of 76 degrees, 80 degrees and 85 degrees, respectively. Subsequently to cutting, the edge surfaces of the planar angled cut tip have been exerted to a finishing process in the form of glass blasting exerted at an angle of 90 degrees relative to the planar end surface of the needle cannula. All tests have been performed at an ambient temperature of 5 deg. Celsius as well as room temperature (20 deg. Celsius) and with a penetration speed corresponding to the speed obtained by triggering an auto-injector such as shown in FIGS. 1-4. No traces of fracturing of the needle cover and the cartridge septum has been observed.

Figure 6:
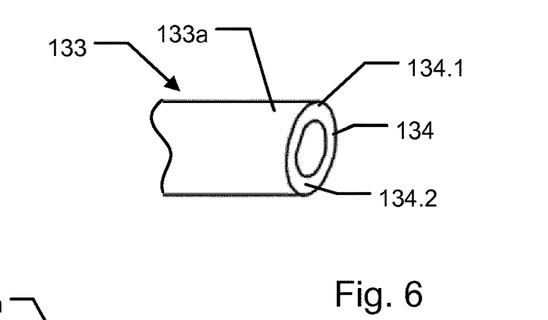
FIG. 6 shows a magnified side view of the proximal portion of such a needle cannula according to the invention.

FIG. 6 shows a magnified side view of the proximal portion of such a needle cannula 130 with an 80 degree cut bevel end. The single cut angled end surface 134 exhibits a leading portion 134.1 defining the most proximal point of the needle cannula. Surface 134 further exhibits a trailing portion 134.2, i.e. a heel portion.

Figure 7:
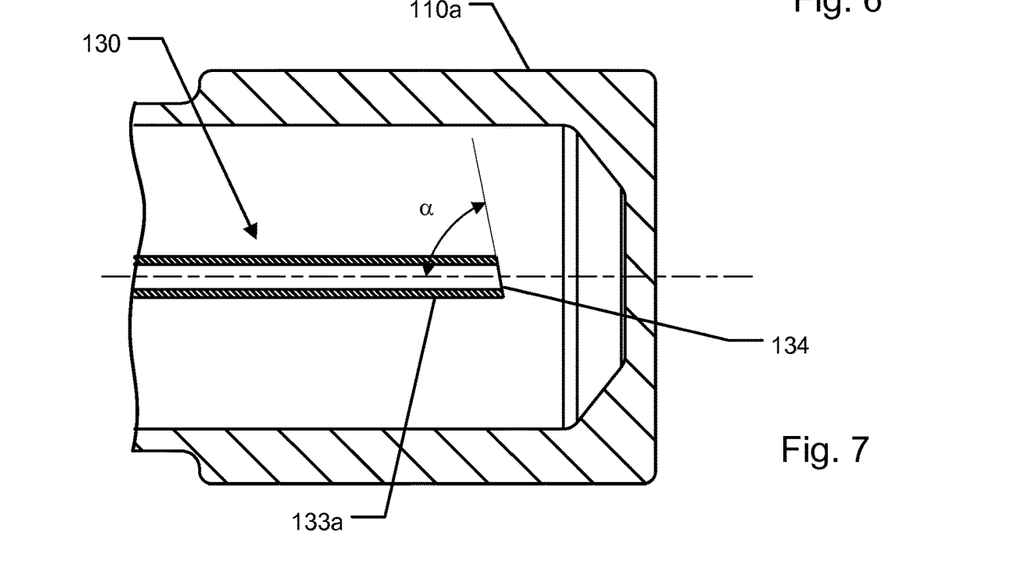
FIG. 7 shows a cross sectional side view of the proximal portion of a needle cannula according to the invention with the proximal needle cover of the injection needle assembly visible, FIGS. 8a, 8b and 8c schematically show manufacturing steps for providing a further exemplary needle cannula according to the invention.

FIG. 7 shows a cross sectional side view of the proximal portion of a needle cannula 130 with an 80 degree cut bevel and with a portion of the proximal needle cover 10a also visible.

The needle cannula according to the invention has proven that the slightly angled bevel surface of needle cannula enables the leading portion 134.1 to provide a well-defined contact point for the needle cannula to establish a connection with the needle cover and the cartridge septum, respectively. The slightly angled grinding surface is proven to be a suitable balance between ensuring the needle indicates where the cover must break by establishing a well-defined tip and not introducing sharp, knife-like structures at locations in the vicinity of the heel portion of the proximal end of the needle cannula. The objective of forming a non-coring needle cannula the grinding is considered effective with a proximal end of the needle cannula exhibiting an angle relative to the central axis within a range from 70-85 degrees.

It is to be noted that, in accordance with the invention, the slightly angled surface may be provided as only covering a fraction of the proximal end surface circumscribing the proximal opening. However, it is contemplated that a main part of the proximal surface, in particular the surface area covering the heel portion is formed with an angle of inclination with respect to the central axis of the needle cannula within said angle interval of 70 to 85 degrees.

The optional subsequent finishing (glass blasting, polishing, etc) is to ensure that no sharp edges, structures or flanges, especially at the "heel" of the needle tube, will potentially cause coring of cooperating cover or seal elements.

Figure 8A:
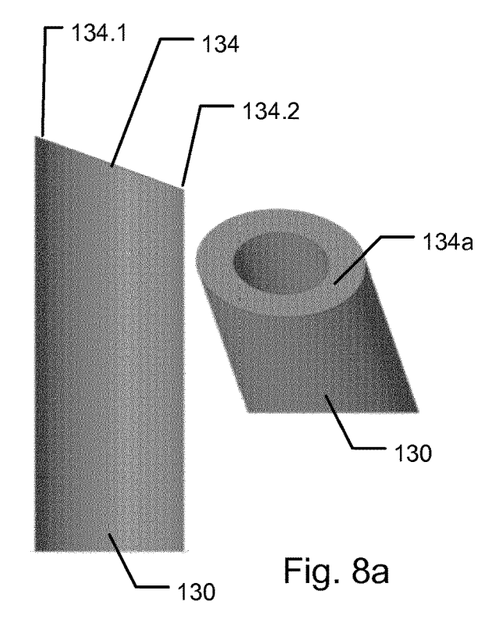
Figure 8B:
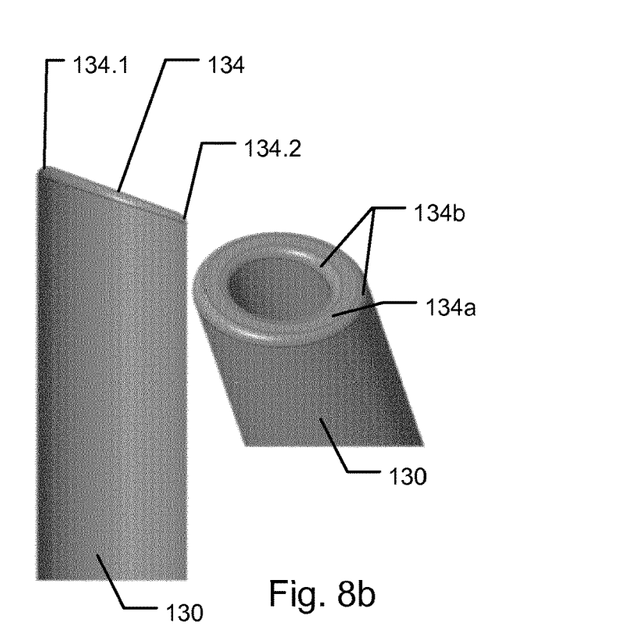
Figure 8C:
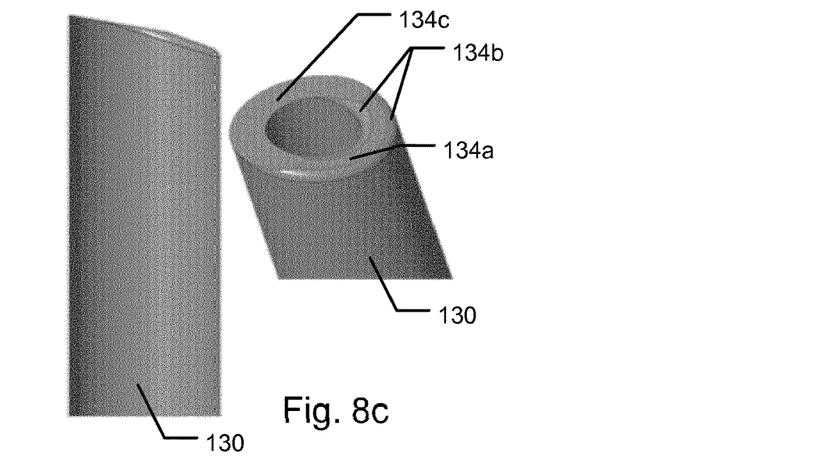

FIGS. 8a to 8c schematically show manufacturing steps for providing a further exemplary needle cannula according to the invention. The proximal portion of such a needle cannula 130 is manufactured in a simple 3-step process. In the shown embodiment, as shown in FIG. 8a, an oblique cut is firstly made to the proximal end 133a of the needle cannula by grinding the needle cannula with a 70 degree grinding angle relative to the central axis. This causes a proximally facing angled surface 134a to be formed which defines a leading portion 134.1 and a heel portion 134.2. In a second procedural step, shown in FIG. 8b, the proximal end of the needle cannula is exerted to a sand blasting operation, or similar blunting operation, so as to cause the initially formed sharp edges to become blunted. Hence, at areas 134b where the angled surface 134a intersects with the sidewall of the cannula 130, the areas 134b form blunted circumferentially running edges, both at edges facing radially inwards and at edges facing radially outwards. In a third procedural step, shown in FIG. 8c a second grinding step is performed by exclusively grinding areas arranged at the leading portion 134.1 of the needle cannula with an 80 degree grinding angle relative to the central axis thereby forming a planar surface portion 134c symmetrically disposed around the leading portion 134.1. Hereby edges disposed only at the leading portion 134.1 are sharpened.

Figure 9:
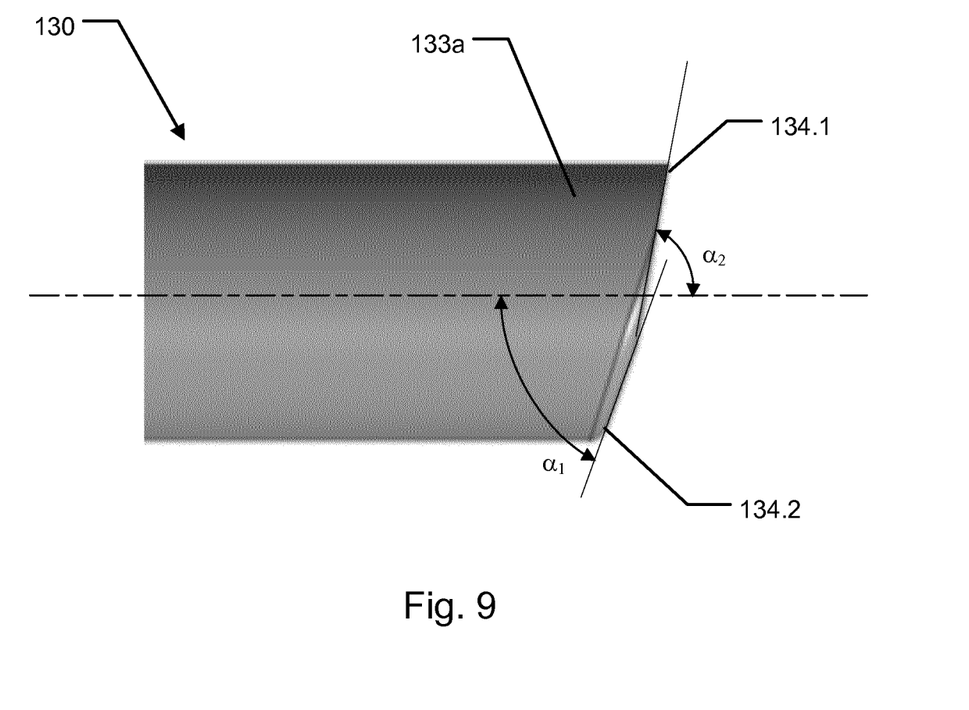
FIG. 9 shows further details of the proximal end of a needle cannula provided by the manufacturing steps shown in FIGS. 8a through 8c.

In the shown embodiment, and further explained with reference to FIG. 9, the first grinding operation may be provided by a grinding angle $\alpha_1$ with respect to the central axis, whereas the second grinding operation may be provided by a grinding angle $\alpha_2$ with respect to the central axis. In further exemplary embodiments, the grinding angle of the first grinding operation may be performed so as to provide a surface portion 134a at the heel portion 134.2 forming an angle $\alpha_1$ within the interval 50 to 75 degrees with respect to the central axis. Typically, in such embodiments, the grinding angle of the second grinding operation may be performed so as to provide a surface portion 134c at the leading portion 134.1 forming an angle $\alpha_2$ with respect to the central axis which is 5 to 10 degrees greater than the angle $\alpha_1$ of surface portion 134a.

By using the simple 3-step operation described above, an inexpensive and effective non-coring solution is provided where the proximal end 133a of the needle cannula 130 exhibits a proximally facing end surface having a sharp leading portion as well as a blunt heel portion.

It is to be noted that, since the distal portion 133b of the needle cannula that carries the skin penetrating tip is very fragile, it is important that this end will be protected during manufacture/assembly, and not used to position the needle. Hence, it is preferable if the proximal portion of the needle 133a can serve this purpose. Hence, the design of the proximal portion of the needle is provided with a robust design allowing positioning of the needle by engaging the proximal portion with a supporting surface until the needle cannula is fixedly attached relative to a needle hub element.

Furthermore, some preferred embodiments have been shown in the foregoing, but it should be stressed that the invention is not limited to these, but may be embodied in other ways within the subject matter defined in the following claims and within the remaining disclosure.

The invention claimed is:

1. An elongated tubular needle cannula for an injection device, the needle cannula extending along a central axis and comprising:
   a skin piercing distal end,
   a proximal end arranged axially opposite the skin piercing distal end, the proximal end being configured for penetrating a seal structure of a medicament container,
   a sidewall extending between the skin piercing distal end and the proximal end, and
   a lumen extending through the needle cannula along said central axis, said lumen has a first opening arranged axially at the skin piercing distal end and a second opening arranged axially at the proximal end, wherein the proximal end being defined by an angled surface pointing proximally, the angled surface intersecting with the sidewall at a proximal-most point defining a leading portion and intersecting with the sidewall at an oppositely arranged trailing portion defining a heel portion,
wherein the angled surface pointing proximally comprises a surface portion at the heel portion forming an angle ($\alpha_1$) between 50 to 75 degrees with respect to the central axis, and further comprises a surface portion at the leading portion forming an angle ($\alpha_2$) between 60 to 85 degrees with respect to the central axis,
wherein said angled surface intersects with the sidewall to define a radially inwards facing circumferential edge and a radially outwards facing circumferential edge, and wherein the radially inwards facing circumferential edge and/or the radially outwards facing circumferential edge is/are blunted along an annular section symmetrically disposed around the heel portion, said annular section having an annular width within 100 to 220 degrees.

2. The elongated tubular needle cannula as defined in claim 1, wherein said surface portion at the heel portion defines at least 20% of said angled surface, and wherein said surface portion at the leading portion defines at least 30% of said angled surface.

3. The elongated tubular needle cannula as defined in claim 1, wherein edges arranged at the leading portion are sharpened.

4. The elongated tubular needle cannula as defined in claim 1, wherein the surface portion at the leading portion forms an angle ($\alpha_2$) with respect to the central axis which is 5 to 10 degrees greater than the angle ($\alpha_1$) of surface portion at the heel portion with respect to the central axis.

5. The elongated tubular needle cannula as defined in claim 1, wherein said surface portion at the heel portion forms an angle ($\alpha_1$) between 55 to 70 degrees with respect to the central axis.

6. The elongated tubular needle cannula as defined in claim 1, wherein the needle cannula is configured for subcutaneous injection, and wherein the needle cannula is a 26 G needle or smaller.

7. The elongated tubular needle cannula as defined in claim 6, wherein the needle cannula is a 27 G needle or smaller.

8. The elongated tubular needle cannula as defined in claim 6, wherein the needle cannula is a 28 G needle or smaller.

9. The elongated tubular needle cannula as defined in claim 6, wherein the needle cannula is a 29 G needle or smaller.

10. The elongated tubular needle cannula as defined in claim 6, wherein the needle cannula is a 30 G needle or smaller.

11. The elongated tubular needle cannula as defined in claim 1, wherein the sidewall of the needle cannula forms an elongated tubular enclosure that does not include opening(s) other than said first opening and said second opening.

12. The elongated tubular needle cannula as defined in claim 1, wherein said annular section has an annular width within 140 to 190 degrees.

13. An injection needle assembly for an injection device, the injection needle assembly comprising:
   a needle hub,
   an elongated tubular needle cannula as defined in claim 1, and
   a first needle cover,
wherein the needle hub holds the needle cannula between the skin piercing distal end and the proximal end such that a distal portion of the needle cannula extends distally from the needle hub and such that a proximal portion of the needle cannula extends proximally from the needle hub towards the proximal end of the needle cannula, and
wherein the first needle cover is mounted on the needle hub and forms an axially extending elongated flexible enclosure which sealingly accommodates the proximal portion of the needle cannula, wherein the first needle cover has a needle hub end mounted relative to the needle hub and a free end extending beyond the proximal end of the needle cannula, the first needle cover being configured to axially collapse and become penetrated by the proximal portion of the needle cannula when a distally directed penetration force is applied on the free end of the first needle cover urging the free end of the first needle cover towards the needle hub.

14. The injection needle assembly as defined in claim 13, wherein the first needle cover is made from silicone rubber.

15. The injection needle assembly as defined in claim 13, further comprises a second needle cover, wherein the second needle cover is mounted on the needle hub and forms an axially extending elongated flexible enclosure which sealingly accommodates the distal portion of the needle cannula, wherein the second needle cover has a needle hub end mounted relative to the needle hub and a free end extending beyond the distal end of the needle cannula, the second needle cover being configured to axially collapse and become penetrated by the distal portion of the needle cannula when a proximally directed penetration force is applied on the free end of the second needle cover urging the free end of the second needle cover towards the needle hub.

16. An injection device, comprising:
a housing defining a distal drug expelling end and an opposite proximal end,
an injection needle assembly as defined in claim 13, the injection needle assembly arranged relative to the housing with the proximal end of the needle cannula pointing towards the proximal end of the housing,
a medicament container containing a medicament, the medicament container comprising a cylindrical body extending along a longitudinal axis arranged coaxially with the central axis of the needle cannula, the medicament container further comprising a seal structure adapted to become penetrated by the proximal portion of the needle cannula enabling expelling of medicament from the medicament container, wherein the medicament container is arranged axially movable relative to the injection needle assembly for moving the medicament container from a first state where the first needle cover and the seal structure are not penetrated by the needle cannula and into a second state where the proximal portion of the needle cannula has penetrated the first needle cover and the seal structure, and
an expelling assembly comprising a strained spring configured to act on the medicament container,
wherein the expelling assembly is activatable to enable the strained spring to move the medicament container from the first state to the second state.

17. The injection device as defined in claim 16, wherein, upon activation of the expelling assembly, the proximal portion of the needle cannula penetrates the seal structure of the medicament container by a relative axial movement with no relative rotation between the needle cannula and the seal structure.

18. The injection device as defined in claim 16, wherein the injection needle assembly comprises a second needle cover mounted on the needle hub and forming an axially extending elongated flexible enclosure which sealingly accommodates the distal portion of the needle cannula, wherein the second needle cover has a needle hub end mounted relative to the needle hub and a free end extending beyond the distal end of the needle cannula, the second needle cover being configured to axially collapse and become penetrated by the distal portion of the needle cannula when a proximally directed penetration force is applied on the free end of the second needle cover urging the free end of the second needle cover towards the needle hub, wherein the injection device comprises a needle shield arranged to shield the second needle cover, and wherein the needle shield and the injection needle assembly is arranged to axially move relative to each other for causing the distal portion of the needle cannula to penetrate the second needle cover and enable the distal portion of the needle cannula to extend beyond a distal end portion of the needle shield.

19. An injection device as defined in claim 16, wherein the seal structure of the medicament container is provided as, or comprises, a non-slit medicament container septum.

20. An elongated tubular needle cannula for an injection device, the needle cannula extending along a central axis and comprising:
a skin piercing distal end,
a proximal end arranged axially opposite the skin piercing distal end, the proximal end being configured for penetrating a seal structure of a medicament container,
a sidewall extending between the skin piercing distal end and the proximal end, and
a lumen extending through the needle cannula along said central axis, said lumen has a first opening arranged axially at the skin piercing distal end and a second opening arranged axially at the proximal end, wherein the proximal end being defined by an angled surface pointing proximally, the angled surface intersecting with the sidewall at a proximal-most point defining a leading portion and intersecting with the sidewall at an oppositely arranged trailing portion defining a heel portion,
wherein the angled surface pointing proximally comprises a surface portion at the heel portion forming an angle ($\alpha_1$) between 50 to 75 degrees with respect to the central axis, and further comprises a surface portion at the leading portion forming an angle ($\alpha_2$) between 60 to 85 degrees with respect to the central axis,
wherein the surface portion at the leading portion forms an angle ($\alpha_2$) with respect to the central axis which is 5 to 10 degrees greater than the angle ($\alpha_1$) of surface portion at the heel portion with respect to the central axis.

21. The elongated tubular needle cannula as defined in claim 20, wherein said surface portion at the heel portion defines at least 20% of said angled surface, and wherein said surface portion at the leading portion defines at least 30% of said angled surface.

22. The elongated tubular needle cannula as defined in claim 20, wherein said angled surface intersects with the sidewall to define a radially inwards facing circumferential edge and a radially outwards facing circumferential edge, and wherein the radially inwards facing circumferential edge and/or the radially outwards facing circumferential edge is/are blunted along an annular section symmetrically disposed around the heel portion, said annular section having an annular width within 100 to 220 degrees.

23. The elongated tubular needle cannula as defined in claim 22, wherein said annular section has an annular width within 140 to 190 degrees.

24. The elongated tubular needle cannula as defined in claim 20, wherein edges arranged at the leading portion are sharpened.

25. The elongated tubular needle cannula as defined in claim 20, wherein said surface portion at the heel portion forms an angle ($\alpha_1$) between 55 to 70 degrees with respect to the central axis.

26. The elongated tubular needle cannula as defined in claim 20, wherein the needle cannula is configured for subcutaneous injection, and wherein the needle cannula is a 26 G needle or smaller.

27. The elongated tubular needle cannula as defined in claim 20, wherein the sidewall of the needle cannula forms an elongated tubular enclosure that does not include opening(s) other than said first opening and said second opening.

28. The elongated tubular needle cannula as defined in claim 26, wherein the needle cannula is a 28 G needle or smaller.

29. The elongated tubular needle cannula as defined in claim 26, wherein the needle cannula is a 29 G needle or smaller.

30. The elongated tubular needle cannula as defined in claim 26, wherein the needle cannula is a 30 G needle or smaller.

31. The elongated tubular needle cannula as defined in claim 26, wherein the needle cannula is a 27 G needle or smaller.

32. An injection needle assembly for an injection device, the injection needle assembly comprising:
   a needle hub,
   an elongated tubular needle cannula as defined in claim 20, and
   a first needle cover,
wherein the needle hub holds the needle cannula between the skin piercing distal end and the proximal end such that a distal portion of the needle cannula extends distally from the needle hub and such that a proximal portion of the needle cannula extends proximally from the needle hub towards the proximal end of the needle cannula, and
wherein the first needle cover is mounted on the needle hub and forms an axially extending elongated flexible enclosure which sealingly accommodates the proximal portion of the needle cannula, wherein the first needle cover has a needle hub end mounted relative to the needle hub and a free end extending beyond the proximal end of the needle cannula, the first needle cover being configured to axially collapse and become penetrated by the proximal portion of the needle cannula when a distally directed penetration force is applied on the free end of the first needle cover urging the free end of the first needle cover towards the needle hub.

33. The injection needle assembly as defined in claim 32, wherein the first needle cover is made from silicone rubber.

34. The injection needle assembly as defined in claim 32, further comprises a second needle cover, wherein the second needle cover is mounted on the needle hub and forms an axially extending elongated flexible enclosure which sealingly accommodates the distal portion of the needle cannula, wherein the second needle cover has a needle hub end mounted relative to the needle hub and a free end extending beyond the distal end of the needle cannula, the second needle cover being configured to axially collapse and become penetrated by the distal portion of the needle cannula when a proximally directed penetration force is applied on the free end of the second needle cover urging the free end of the second needle cover towards the needle hub.

35. An injection device, comprising:
   a housing defining a distal drug expelling end and an opposite proximal end,
   an injection needle assembly as defined in claim 32, the injection needle assembly arranged relative to the housing with the proximal end of the needle cannula pointing towards the proximal end of the housing,
   a medicament container containing a medicament, the medicament container comprising a cylindrical body extending along a longitudinal axis arranged coaxially with the central axis of the needle cannula, the medicament container further comprising a seal structure adapted to become penetrated by the proximal portion of the needle cannula enabling expelling of medicament from the medicament container, wherein the medicament container is arranged axially movable relative to the injection needle assembly for moving the medicament container from a first state where the first needle cover and the seal structure are not penetrated by the needle cannula and into a second state where the proximal portion of the needle cannula has penetrated the first needle cover and the seal structure, and
   an expelling assembly comprising a strained spring configured to act on the medicament container,
wherein the expelling assembly is activatable to enable the strained spring to move the medicament container from the first state to the second state.

36. The injection device as defined in claim 35, wherein, upon activation of the expelling assembly, the proximal portion of the needle cannula penetrates the seal structure of the medicament container by a relative axial movement with no relative rotation between the needle cannula and the seal structure.

37. The injection device as defined in claim 35, wherein the injection needle assembly comprises a second needle cover mounted on the needle hub and forming an axially extending elongated flexible enclosure which sealingly accommodates the distal portion of the needle cannula, wherein the second needle cover has a needle hub end mounted relative to the needle hub and a free end extending beyond the distal end of the needle cannula, the second needle cover being configured to axially collapse and become penetrated by the distal portion of the needle cannula when a proximally directed penetration force is applied on the free end of the second needle cover urging the free end of the second needle cover towards the needle hub, wherein the injection device comprises a needle shield arranged to shield the second needle cover, and wherein the needle shield and the injection needle assembly is arranged to axially move relative to each other for causing the distal portion of the needle cannula to penetrate the second needle cover and enable the distal portion of the needle cannula to extend beyond a distal end portion of the needle shield.

38. An injection device as defined in claim 35, wherein the seal structure of the medicament container is provided as, or comprises, a non-slit medicament container septum.

* * * * *